US012589059B2

(12) United States Patent
Maron et al.

(10) Patent No.:  US 12,589,059 B2
(45) Date of Patent:  Mar. 31, 2026

(54) MINERAL SUNSCREEN COMPOSITIONS WITH HIGH SPF AND SHELF STABILITY

(71) Applicant: L'OREAL, Paris (FR)

(72) Inventors: Zachary Maron, Jersey City, NJ (US);
Brian Bodnar, Manasquan, NJ (US);
Anil Shah, East Windsor, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/490,652

(22) Filed: Sep. 30, 2021

(65) Prior Publication Data

US 2023/0121763 A1    Apr. 20, 2023

(51) Int. Cl.
| | |
|---|---|
| *A61K 8/06* | (2006.01) |
| *A61K 8/27* | (2006.01) |
| *A61K 8/29* | (2006.01) |
| *A61K 8/34* | (2006.01) |
| *A61K 8/362* | (2006.01) |
| *A61K 8/37* | (2006.01) |
| *A61K 8/58* | (2006.01) |
| *A61K 8/73* | (2006.01) |
| *A61K 8/81* | (2006.01) |
| *A61K 8/92* | (2006.01) |
| *A61Q 17/04* | (2006.01) |

(52) U.S. Cl.
CPC ................ *A61K 8/062* (2013.01); *A61K 8/27* (2013.01); *A61K 8/29* (2013.01); *A61K 8/345* (2013.01); *A61K 8/362* (2013.01); *A61K 8/37* (2013.01); *A61K 8/585* (2013.01); *A61K 8/737* (2013.01); *A61K 8/8152* (2013.01); *A61K 8/92* (2013.01); *A61Q 17/04* (2013.01); *A61K 2800/48* (2013.01); *A61K 2800/52* (2013.01); *A61K 2800/594* (2013.01)

(58) Field of Classification Search
CPC . A61K 8/062; A61K 8/27; A61K 8/29; A61K 8/37; A61K 8/39; A61K 8/86; A61K 8/92; A61K 8/345; A61K 8/362; A61K 8/585; A61K 8/737; A61K 8/8152; A61K 2800/48; A61K 2800/52; A61K 2800/594; A61Q 17/04
See application file for complete search history.

(56) References Cited

U.S. PATENT DOCUMENTS

| | | | |
|---|---|---|---|
| 2002/0012640 A1* | 1/2002 | Mohammadi .......... | A61Q 17/04 424/59 |
| 2006/0078514 A1* | 4/2006 | Bertz ..................... | A61Q 17/04 424/59 |
| 2007/0264204 A1* | 11/2007 | Noor ...................... | A61K 8/585 424/47 |
| 2011/0256192 A1* | 10/2011 | Chevalier .............. | A61Q 17/04 424/59 |

| | | | |
|---|---|---|---|
| 2014/0205551 A1* | 7/2014 | Mendrok-Edinger ....................... | A61K 8/496 424/59 |
| 2016/0120786 A1 | 5/2016 | Halpern Chirch et al. | |
| 2020/0276093 A1* | 9/2020 | Farran ................... | A61K 8/8152 |
| 2020/0281829 A1 | 9/2020 | Guiramand et al. | |
| 2021/0093529 A1 | 4/2021 | LaRosa et al. | |
| 2021/0177719 A1 | 6/2021 | Lorant et al. | |
| 2023/0025603 A1* | 1/2023 | Hamazaki .............. | A61Q 17/04 |

FOREIGN PATENT DOCUMENTS

| | | |
|---|---|---|
| EP | 1760738 A1 | 3/2007 |
| FR | 2983718 A1 | 6/2013 |

OTHER PUBLICATIONS

Rocryl 420 Hydroxyethyl Acrylate: https://www.dow.com/en-us/pdp.rocryl-420-hydroxyethyl-acrylate-hea.202524z.html#overview. (Year: 2025).*
2-Hydroxyethyl acrylate: https://polysciences.com/products/2-hydroxyethyl-acrylate?srsltid=AfmBOooV8ncT4kaZR1iuBpdm48LjlacJpXLTIPy09F7lGa0hEh4zylmD. (Year: 2025).*
Meaudre et al.: https://www.lorealdermatologicalbeauty.com/inter/skinalliance/posters/wcd-posters/photoprotection/wcd-2023-innovation-in-uv-protection-when-it-becomes-a-daily-must-have. (Year: 2023).*
Search Report issued to French counterpart Application No. FR2113459 dated Aug. 19, 2022.
Anonymous, Mintel "Body Sun Protector SPF 30," XP 055949256, No. 2809257, www.gnpd.com.
Anonymous "Aqua Multi-Effect UV Lotion SPF 50+ PA++++," XP055949256, No. 8621513, www.gnpd.com.
Anonymous, Mintel, "SPF 45 Face Sunscreen," XP055949261, No. 1310595, www.gnpd.com.
PCT Notification of Transmittal of the International Search Report and the Written Opinion of the International Searching Authority, or the Declaration issued to counterpart Application No. PCT/IB2022/059053 dated Dec. 9, 2022.
"Pemulen TR-1 polymer", The Lubrizol Corporation, https://www.lubrizol.com/Personal-Care/Products/Product-Finder/Products-Data/Pemulen-TR-1-polymer (retrieved Aug. 3, 2023).
"Introducing Pemulen Polymeric Emulsifiers", The Lubrizol Corporation, Oct. 15, 2007.

* cited by examiner

*Primary Examiner* — Hong Yu
(74) *Attorney, Agent, or Firm* — McNees Wallace & Nurick

(57) ABSTRACT

A sunscreen composition is an oil-in-water emulsion of aqueous and oil phases and includes at least one lipophilic acrylate-based oil thickener, at least one mineral UV filter, and at least one nonionic surfactant that is a polyethylene glycol ethers of fatty acids or polyethylene glycol esters of fatty acids, or a combination thereof. The sunscreen composition may also include one or a combination of ingredients selected from the group consisting of solvents, SPF boosters, humectants, skin care actives, oils, waxes, thickeners, preservatives, pH adjusters, chelating agents, viscosity adjusters, cooling agents, fillers, fragrances, dyes, pigments, and combinations thereof. The sunscreen composition has an SPF in a range from about 30 to about 55 and exhibits phase stability and processibility.

17 Claims, No Drawings

MINERAL SUNSCREEN COMPOSITIONS WITH HIGH SPF AND SHELF STABILITY

FIELD OF THE DISCLOSURE

The instant disclosure is directed to sunscreen compositions, and to methods for using the sunscreen compositions to protect keratinous substrates such as skin and hair from UV radiation.

BACKGROUND

The negative effects of exposure to ultraviolet ("UV") light are well known. Prolonged exposure to sunlight causes damage such as sunburn to the skin and dries out hair making it brittle. When skin is exposed to UV light having a wavelength of from about 290 nm to about 400 nm, long term damage can lead to serious conditions such as skin cancer.

UV light also contributes to aging by causing free radicals to form in the skin. Free radicals include, for example, singlet oxygen, hydroxyl radical, the superoxide anion, nitric oxide, and hydrogen radicals. Free radicals attack DNA, membrane lipids and proteins, generating carbon radicals. These in turn react with oxygen to produce a peroxyl radical that can attack adjacent fatty acids to generate new carbon radicals. This cascade leads to a chain reaction producing lipid peroxidation products. Damage to the cell membrane results in loss of cell permeability, increased intercellular ionic concentration, and decreased ability to excrete or detoxify waste products. The end result is a loss of skin elasticity and the appearance of wrinkles. This process is commonly referred to as photo-aging.

Sunscreens can be used to protect against UV damage and delay the signs of photo-aging. The degree of UV protection afforded by a sunscreen composition is directly related to the amount and type of UV filters contained therein. The higher the amount of UV filters, the greater the degree of UV protection. Consumers prefer sunscreen compositions to include natural and not irritating components that appear natural (unnoticeable) once applied. It is known in the art to that there are challenges to providing mineral-based sunscreen products having a high Sun Protection Factor (SPF) that are shelf stable and are capable of maintaining SPF benefit.

The inventors of the instant disclosure have formulated a mineral-based sunscreen which unexpectedly exhibit high SPF and high emulsion structural stability in the presence of high amounts of mineral-based sunscreens that also confer good aesthetics.

SUMMARY OF THE INVENTION

The instant disclosure provides a sunscreen composition that includes mineral UV filtering agents, which are known to be non-irritating, natural, and gentle to the skin, together with oil based acrylate thickeners and nonionic surfactants that confers stable sun protection and emulsion structural stability in the presence of high amounts of mineral UV filters. The sunscreen composition overcomes challenges known in the art wherein high levels of mineral UV filters have been shown to be unstable, as further described herein. The sunscreen composition may optionally include organic UV filters.

In various embodiments, the sunscreen composition includes nonionic surfactants that are selected from polyethylene glycol ethers of fatty acids or polyethylene glycol esters of fatty acids to provide a composition that unexpectedly can be stably prepared at commercial scale and demonstrates SPF and emulsion structural stability that exceeds what has been observed with similar compositions that include mineral sun filters and lipophilic acrylate-based oil thickeners without the selected surfactants. The sunscreen composition has an in vivo tested SPF value of 50 or greater.

In a representative embodiment, the sunscreen composition comprises: an oil-in-water emulsion of aqueous and oil phases, comprising the following components:
- (i) at least one lipophilic acrylate-based oil thickener,
- (ii) at least one mineral UV filter,
- (iii) at least one nonionic surfactant selected from the group consisting of polyethylene glycol ethers of fatty acids, polyethylene glycol esters of fatty acids, and combinations thereof wherein the formula has an SPF in a range from about 30 to about 55 and exhibits phase stability and processibility.

In some embodiments, the sunscreen composition comprises one or more non-mineral UV filters selected organic UV filters.

In some particular embodiments, the sunscreen composition comprises: an oil-in-water emulsion of aqueous and oil phases, comprising the following components:
- (i) at least one lipophilic acrylate-based oil thickener, present from about 0.5% to about 5%;
- (ii) at least one mineral UV filter, present from about 1% to about 25%; and
- (iii) at least one nonionic surfactant selected from the group consisting of polyethylene glycol ethers, polyethylene glycol esters of fatty acids, and combinations thereof, present from at least about 0.1% to about 5%, wherein the components are present by weight, based on the total weight of the sunscreen composition.

In some particular embodiments, the sunscreen composition comprises: an oil-in-water emulsion of aqueous and oil phases, comprising the following components:
- (i) at least one lipophilic acrylate-based oil thickener, present from about 0.75% to about 3%;
- (ii) at least one mineral UV filter, present from about 5% to about 15%; and
- (iii) at least one nonionic surfactant selected from the group consisting of polyethylene glycol ethers, polyethylene glycol esters of fatty acids, and combinations thereof, present from at least about 0.2% to about 3%, wherein the components are present by weight, based on the total weight of the sunscreen composition.

In some particular embodiments, the sunscreen composition comprises: an oil-in-water emulsion of aqueous and oil phases, comprising the following components:
- (i) at least one or more lipophilic acrylate-based oil thickener, present at about 1.8%;
- (ii) at least one mineral UV filter, present at about 7%;
- (iii) at least one or more nonionic surfactant selected from the group consisting of polyethylene glycol ethers, polyethylene glycol esters of fatty acids, and combinations thereof, present in a total amount of about 2%;
- (iv) at least one or more organic UV filters, present in a total amount of about 18%; and
- (v) one or a combination of solvents, wherein the components are present by weight, based on the total weight of the sunscreen composition.

In some particular embodiments, the sunscreen composition comprises: an oil-in-water emulsion of aqueous and oil phases, comprising the following components:

(i) at least one or more lipophilic acrylate-based oil thickener comprising C12-22 alkyl acrylate/hydroxyethylacrylate copolymer;

(ii) at least one mineral UV filter selected from the group consisting of zinc oxide, a zinc oxide derivative, titanium dioxide, a titanium dioxide derivative, and combinations thereof;

(iii) at least one or more nonionic surfactant selected from the group consisting of steareth-2, steareth-20, and combinations thereof;

(iv) at least one or more organic UV filters selected from the group consisting of homosalate, octisalate and octocrylene, and combinations thereof; and (v) one or a combination of additives selected from the group consisting of glycerin, propanediol, ethylhexyl methoxycrylene, butyloctyl salicylate, dicaprylyl carbonate, dicaprylyl ether, isopropyl palmitate, diethylhexyl syringylidenemalonate, trisodium ethylenediamine disuccinate, hydroxyacetophenone, citric acid, coco-caprylate/caprate, Oryza sativa cera, candelilla wax, sunflower seed wax, carnauba wax, polyhydroxystearic acid, xanthan gum, chlorphenesin, and combinations thereof.

In some embodiments, the at least one lipophilic acrylate-based oil thickener comprises an interlimer polymer. In some embodiments the at least one lipophilic acrylate-based oil thickener comprises C12-22 alkyl acrylate/hydroxyethylacrylate copolymer.

In some embodiments, the at least one nonionic surfactant selected from the group consisting of polyethylene glycol ethers, polyethylene glycol esters of fatty acids comprises steareth-2, steareth-20, or a combination thereof. In some embodiments, the at least one nonionic surfactant selected from the group consisting of polyethylene glycol ethers, polyethylene glycol esters of fatty acids comprises steareth-2 and steareth-20.

In some embodiments, the at least one mineral UV filter comprises zinc oxide, a zinc oxide derivative, titanium dioxide, a titanium dioxide derivative, or combinations thereof.

In the various embodiments, the sunscreen composition comprises one or a combination of organic UV filters, and one or a combination of inorganic/mineral UV filters. In some particular embodiments, the inorganic/mineral UV filters include zinc oxide and the optional organic UV filters include each of homosalate, octisalate and octocrylene.

In some embodiments of the sunscreen composition that comprise organic UV filters, the combination of organic and inorganic/mineral UV filters is present in the sunscreen composition in a total amount the range from about 15% to about 45%, or from about 20% to about 25%, based on the total weight of the sunscreen composition.

In some embodiments of the sunscreen composition, the combination of organic and inorganic/mineral UV filters includes zinc oxide present in an amount in the range from about 5% to about 10%, and a blend of organic UV filters comprising homosalate present in an amount in the range from about 5% to about 15%, octisalate present in an amount in the range from about 1% to about 7%, and octocrylene present in an amount in the range from about 7% to about 15%, each present by weight based on the total weight of the sunscreen composition.

In some embodiments, the components of the aqueous phase and the components of the oil phase, respectively, are present in the sunscreen composition at a weight ratio of aqueous components to oil components in a range from about >1:1. In some embodiments, a phase ratio of the aqueous phase to the non-aqueous phase is calculated based on the total weight of the aqueous phase components to the weight of non-aqueous components of the oil phase.

In some embodiments, the sunscreen composition also includes one or more SPF boosters, one or more sensorial fatty compounds or feel modifying powders, or one or more actives.

In some embodiments, the sunscreen composition further comprises one or a combination of additives selected from the group consisting of solvents, SPF boosters, humectants, waxes, skin care actives, oils, thickeners, preservatives, pH adjusters, chelating agents, viscosity adjusters, cooling agents, fillers, fragrances, dyes, pigments, and combinations thereof.

In some particular embodiments, the sunscreen composition further comprises one or more additives selected from the group consisting of glycerin, propanediol, ethylhexyl methoxycrylene, butyloctyl salicylate, dicaprylyl carbonate, dicaprylyl ether, isopropyl palmitate, diethylhexyl syringylidenemalonate, trisodium ethylenediamine disuccinate, hydroxyacetophenone, citric acid, coco-caprylate/caprate, Oryza sativa cera, candelilla wax, sunflower seed wax, carnauba wax, polyhydroxystearic acid, xanthan gum, chlorphenesin, and combinations thereof.

In the various embodiments, the sunscreen composition demonstrates emulsion structural stability wherein the sunscreen composition does not exhibit signs of phase separation, and/or become inhomogeneous after up to 12 weeks in an ambient temperature in the range from about 25° C. up to and including about 45° C., and maintains processibility wherein the sun screen composition can be produced at commercial scale characterized by a production volume of at least 15 kilograms without loss of emulsion structural stability. In the various embodiments, the sunscreen composition demonstrates an SPF (in vivo) in a range from about 30 to about 55. In some embodiments, the sunscreen composition has an SPF of about 30, or of about 45, or of about 50.

In various embodiments, the sunscreen composition may exclude one or more ingredients selected from the group consisting of gemini surfactants, anionic gelling agents, Aristoflex polymers, pigments, iron oxides, and combinations thereof.

The instant disclosure also relates to methods for protecting skin from UV radiation comprising applying an effective amount of the sunscreen composition disclosed in the present case to the skin.

DETAILED DESCRIPTION OF THE DISCLOSURE

Where the following terms are used in this specification, they are used as defined below.

The term "active material" as used herein with respect to the percent amount of an ingredient or raw material, refers to 100% activity of the ingredient or raw material, unless otherwise specified.

The terms "aqueous phase" and "water phase" mean water, water soluble, water miscible and water dispersible ingredients, and represents the sum total of all ingredients in the composition which are water-soluble or water-dispersible, and which are combined together with water during the preparation of the example emulsion compositions.

"Cosmetically acceptable" means that the item in question is compatible with a keratinous substrate such as skin and hair. For example, a "cosmetically acceptable carrier" means a carrier that is compatible with a keratinous substrate such as skin and hair.

The term "Homogenous" means in reference to the composition as having the visual appearance of being substantially uniform throughout, i.e., visually lacks separation and pooling of fluid.

The term "keratinous tissue" includes, but is not limited to, skin, hair, and nails.

The term "mineral UV filtering agent" is interchangeable with the terms "mineral UV screening agent," "inorganic UV filtering agent," "inorganic UV screening agent," "mineral UV filter, and "inorganic UV filter." Mineral UV filtering agents are compounds that do not include any carbon atoms in their chemical structures that are capable of screening out, scattering, or absorbing UV radiation between 280 and 400 nm.

The term "oil thickening" means any raw material which when combined with the oil phase of the emulsion results in a thickening action on said oil phase.

The term "polymers," as defined herein, include homopolymers and copolymers formed from at least two different types of monomers.

The term "processibility" refers to the demonstrated suitability of the sunscreen composition to be produced at commercial scale characterized by a production volume of at least 15 kilograms wherein the sunscreen composition maintains emulsion structural stability as defined herein to provide a generally homogenous, usable formula, that maintains emulsion structural stability.

The term "SPF booster" refers to a material which increases the UV absorption of another material when the two are intermixed in a composition by refracting UV radiation, thereby increasing the effective path length of the UV radiation through the sunscreen composition.

The term "emulsion structural stability" refers to the oil-in-water emulsion structural stability and means that the sunscreen composition exhibits an initially good aesthetic appearance, including lack of a grainy texture, lack of crystal formation, maintains consistent microscopic structure, and does not demonstrate visually perceptible separation of phases, appreciable pooling of fluid, or droplet formation. In addition, the sunscreen composition retains emulsion structural stability as described above, and maintains consistent color, odor, and viscosity during extended storage including storage up to 12 weeks, in particular after exposure to an ambient temperature from as low as about 25° C. up to about 45° C. For example, a sunscreen composition is considered to demonstrate stability of the emulsion structural if the sunscreen composition does not exhibit signs of phase separation, and/or become inhomogeneous after up to 12 weeks in an ambient temperature in the range from about 25° C. up to and including about 45° C.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, less than about 0.01 wt. %, or none of the specified material.

The term "sun protection factor" or "SPF" is a value expressed mathematically by the ratio of the irradiation time necessary to attain the erythemogenic threshold with the UV screening agent to the time necessary to attain the erythemogenic threshold without UV screening agent. SPF generally provides information about the skin's resistance to ultraviolet B (UVB) radiation from the sun. The SPF rating system has been developed to provide consumer guidance in selecting sunscreens. The sunscreen composition according to the present disclosure can be formulated to achieve a variety of different SPFs. For example, the sunscreen composition can have an in vivo SPF of at least 30, 35, 40, 45, 50, or 55 or higher (or in a range between any of these values). As demonstrated herein, in some embodiments, the sunscreen composition has an SPF that is at least 50 or greater, measured as defined by FDA 2011 SPF testing method and/or on a tested subject.

The term "water-in-oil emulsion" or "W/O emulsion" includes a water phase dispersed in an oil phase, where the oil phase is a continuous phase.

The instant disclosure relates to a sunscreen composition and embodiments thereof which provide a high degree of sun protection and emulsion structural stability and processability, the sunscreen composition comprising mineral UV filters with or without non-mineral UV filters and oil-based acrylate thickeners, and nonionic surfactants selected from polyethylene glycol ethers of fatty acids and polyethylene glycol esters of fatty acids in an oil-in-water emulsion form.

It is known in the art that stable performing sunscreen compositions can be provided that include lipophilic acrylate-based oil thickener and non-mineral UV filters, however, the inventors have shown that upon addition of mineral UV filters, the compositions failed to result in stable, performing compositions particularly when high levels of mineral UV filters were incorporated.

The inventors have provided a composition that unexpectedly provides for a stable, processible, high SPF sunscreen composition which comprise mineral UV filters with or without non-mineral UV filters using oil-based acrylate thickeners and nonionic surfactants selected from polyethylene glycol ethers of fatty acids and polyethylene glycol esters of fatty acids.

As exemplified herein below, the inventors have shown that the sunscreen composition which comprises mineral UV filters with or without non-mineral UV filters and oil-based acrylate thickeners that are otherwise unstable and/or have lower sun protection can be rendered stable and processible at commercial production volumes by incorporating nonionic surfactants selected from polyethylene glycol ethers of fatty acids and polyethylene glycol esters of fatty acids. The sunscreen composition demonstrates processibility that is in contrast to compositions that include the same content of mineral and organic UV filters as the sunscreen composition but do not include an nonionic surfactant selected from the group consisting of polyethylene glycol ethers, polyethylene glycol esters of fatty acids, and combinations thereof. As shown in the examples herein, such compositions that include mineral based UV filters are not processible at or over production volume of about 15 kilograms or greater.

Lipophilic Acrylate-Based Oil Thickener

In various embodiments, the sunscreen composition comprises at least one lipophilic acrylate-based oil thickener. According to one more particular embodiment of the present disclosure, the at least one lipophilic acrylate-based oil thickener is derived from a monomer containing a crystallizable chain chosen from saturated C14 to C22 alkyl (meth)acrylates and even more particularly poly(stearyl acrylate) or poly(behenyl acrylate).

As particular examples of a lipophilic acrylate-based oil thickener that may be used in the sunscreen composition according to the present disclosure, mention may be made of polymers having the INCI name "Poly C10-C30 alkyl acrylate", for instance the Intelimer™ products from the company Air Products, for instance the product Intelimer H4. Other examples include the product Intelimer (TM) IPA 13-1, or the product Intelimer (TM) IPA 13-6. More generally, the lipophilic acrylate-based oil thickener may be a polymer as disclosed according to US Patent Application Publication number US20070264204, which discloses a broad range of functionalized side chain crystalline (SCC) polymers can be used to thicken oils, provided that the SCC polymer will dissolve in the oil at a temperature above the crystalline melting point of the polymer (referred to herein as Tp) and can crystallize when the solution of the polymer in the oil is cooled to a temperature which is below Tp and at which the thickened oil composition is to be used.

In some particular embodiments, the at least one lipophilic acrylate-based oil thickener comprises C12-22 alkyl acrylate/hydroxyethylacrylate copolymer.

Each one of the at least one lipophilic acrylate-based oil thickener is present in the sunscreen composition at a concentration from about 0.5% to about 5%, in some embodiments from about 0.75% to 3%, and in some embodiments from about 1% to 2% by weight, all weights based on the total weight of the sunscreen composition. Thus, in various embodiments, a lipophilic acrylate-based oil thickener is present in the sunscreen composition in a weight percent amount from 0.05, 0.06, 0.07, 0.08, 0.09, 1.0, 2.0, 3.0, 4.0, to 5.0 percent by weight, including increments there between.

Nonionic Surfactant

In various embodiments, the sunscreen composition comprises at least one nonionic surfactant chosen from polyethylene glycol ethers of fatty acids, polyethylene glycol esters of fatty acids, or combinations thereof.

In some embodiments, the at least one nonionic surfactant selected from the group consisting of polyethylene glycol ethers, polyethylene glycol esters of fatty acids comprises steareth-2, steareth-20, or a combination thereof. In some embodiments, the at least one nonionic surfactant selected from the group consisting of polyethylene glycol ethers, polyethylene glycol esters of fatty acids comprises steareth-2 and steareth-20. In some embodiments, steareth-2 is present from about 0.2% to about 0.6%, or at about 0.4% to about 0.5%, and steareth-20 is present from about 1.2% to about 1.6%, or at about 0.8% to about 1.5%, all amounts by weight based on the total weight of the sunscreen composition.

Each one of the at least one nonionic surfactant chosen from polyethylene glycol ethers of fatty acids or polyethylene glycol esters of fatty acids is present in the sunscreen composition at a concentration from about 0.1% to about 5%, in some embodiments from about 0.2% to 3%, and in some embodiments from about 1.5% to 2.5% by weight, all weights based on the total weight of the sunscreen composition. Thus, in various embodiments, a nonionic surfactant chosen from polyethylene glycol ethers of fatty acids or polyethylene glycol esters of fatty acids is present in the sunscreen composition in a weight percent amount from 0.1, 0.2, 0.3, 0.4, 0.5, 0.6, 0.7, 0.8, 0.9, 1.0, 2.0, 3.0, 4.0, to 5.0 percent by weight, including increments there between.

UV Filters

In accordance with the various embodiments, the sunscreen composition according to the disclosure includes at least one inorganic/mineral based. In some embodiments, the sunscreen composition may also include one or more organic UV filters. The organic UV filters, when present, are typically present in the oil phase of the emulsion.

In some embodiments, the sunscreen composition includes zinc oxide and may optionally include one or a combination of organic UV filters selected from homosalate, octisalate (ethylhexyl salicylate), octocrylene and combinations of these. In some embodiments, the sunscreen composition includes each of octisalate, homosalate, octocrylene in addition to the inorganic/mineral based UV filter.

In some particular embodiments, the sunscreen composition excludes, or is free from or devoid of organic UV filters. In some particular embodiments, the sunscreen composition excludes, or is free from or devoid of organic UV filters selected from oxybenzone and octinoxate organic UV filters.

In some embodiments, the one or more mineral UV filtering agents are selected from the group consisting of titanium dioxide, zinc oxide, iron oxides, cerium oxides, zirconium oxides, and combinations thereof. In some embodiments, the at least one mineral UV filter comprises zinc oxide, a zinc oxide derivative, titanium dioxide, a titanium dioxide derivative, or combinations thereof.

In some embodiments, the sunscreen composition comprises one or a combination of organic UV filters, and one or a combination of inorganic/mineral UV filters. In some particular embodiments, the inorganic/mineral UV filters include zinc oxide and the optional organic UV filters include each of homosalate, octisalate and octocrylene.

In some embodiments of the sunscreen composition, the inorganic/mineral UV filter is present in an amount in a range from about 1% to about 25%, or from about 5% to about 15%, or from about 5% to about 15%, 6.5% to about 7.5%, each present by weight based on the total weight of the sunscreen composition. Thus, an inorganic/mineral UV filter may be present in the sunscreen composition, by weight, based on the total weight of the sunscreen composition, from about 1, 2, 3, 4, 5, 6, 7, 8, 9, 10, 11, 12, 13, 14, 15, 16, 17, 18, 19, 20, 21, 22, 23, 24, to about 25 weight percent, including increments and ranges therein and there between.

In some embodiments of the sunscreen composition, the combination of organic and inorganic/mineral UV filters includes zinc oxide present in an amount in the range from about 5% to about 10%, and a blend of organic UV filters comprising homosalate present in an amount in the range from about 5% to about 15%, octisalate present in an amount in the range from about 1% to about 7%, and octocrylene present in an amount in the range from about 7% to about 15%, each present by weight based on the total weight of the sunscreen composition. Thus, an organic UV filter may be present in the sunscreen composition, by weight, based on the total weight of the sunscreen composition, from about 1, 2, 3, 4, 5, 6, 7, 8, 9, 10, 11, 12, 13, 14, 15, 16, 17, 18, 19 to about 20 weight percent, including increments and ranges therein and there between.

In some embodiments of the sunscreen composition that comprise organic UV filters, the combination of organic and inorganic/mineral UV filters is present in the sunscreen composition in a total amount the range from about 15% to about 45%, or from about 20% to about 25%, based on the total weight of the sunscreen composition.

Thus, when organic UV filters are present, the combination of UV filters present, by weight, based on the total weight of the sunscreen composition, is from about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 to about 45 weight percent, including increments and ranges therein and there between.

Inorganic/Mineral UV Filters

In various embodiments, the sunscreen composition comprises one or a combination of inorganic UV filters. The inorganic UV filter used for the present disclosure may be active in the UV-A and/or UV-B region. The inorganic UV filter may be hydrophilic and/or lipophilic. The inorganic UV filter is, in some embodiments, insoluble in solvents, such as water, and ethanol commonly used in cosmetics.

The inorganic UV filter be in the form of a fine particle such that the mean (primary) particle diameter thereof ranges from 1 nm to 50 nm, and in some embodiments 5 nm to 40 nm, and in some embodiments 10 nm to 30 nm. The mean (primary) particle size or mean (primary) particle diameter herein is an arithmetic mean diameter. In some embodiments, a particle may have a diameter that is has a mean particle size that is about or less than about 1 micron, or that is about or less than about 200 nm, or that is about or less than about 100 nm (sometimes referred to nanoscale). It will be understood by one of ordinary skill in the art that a particle that is referred to as nano scale for purposes of cosmetic applications including for the sunscreen composition according to this disclosure will have a mean particle size that is less than about 100 nm unless specifically identified otherwise, for example as in the case of nano zinc oxide which is sometimes referred to as nanoscale though the UV agent has a mean primary particle size that is less than 200 nm.

The inorganic UV filter can be selected from the group consisting of silicon carbide, metal oxides, which may or may not be coated, and mixtures thereof. And in some embodiments, the inorganic UV filters are selected from pigments formed of metal oxides, such as, for example, pigments formed of titanium oxide (amorphous or crystalline in the rutile and/or anatase form), iron oxide, zinc oxide, zirconium oxide, or cerium oxide, which are all UV photoprotective agents that are well known per se.

The inorganic UV filter may or may not be coated. The inorganic UV filter may have one or more coating. The coating may comprise one or more compound selected from the group consisting of alumina, silica, aluminum hydroxide, silicones, silanes, fatty acids, or salts thereof (such as sodium, potassium, zinc, iron, or aluminum salts), fatty alcohols, lecithin, amino acids, polysaccharides, proteins, alkanolamines, waxes, such as beeswax, (meth)acrylic polymers, organic UV filters, and (per) fluoro compounds. It is in some embodiments desirable for the coating to include one or a combination of organic UV filter.

Of course, the inorganic UV filter made of metal oxides may, before their treatment with silicones, have been treated with other surfacing agents, in particular, with cerium oxide, alumina, silica, aluminum compounds, silicon compounds, or their mixtures. The coated inorganic UV filter may have been prepared by subjecting the inorganic UV filter to one or more surface treatments of a chemical, electronic, mechano-chemical, and/or mechanical nature with any of the compounds as described above, as well as polyethylenes, metal alkoxides (titanium or aluminum alkoxides), metal oxides, sodium hexametaphosphate, and those shown, for example, in Cosmetics & Toiletries, February 1990, Vol. 105, pp. 53-64.

The coated inorganic UV filter may be titanium oxides coated: with silica, such as the product "Sun veil" from Ikeda, and "Sunsil TIN 50" from Sunjin Chemical; with silica and with iron oxide, such as the product "Sunveil F" from Ikeda; with silica and with alumina, such as the products "Microtitanium Dioxide MT 500 SA" from Tayca, "Tioveil" from Tioxide, and "Mirasun TiW 60" from Rhodia; with alumina, such as the products "Tipaque TTO-55 (B)" and "Tipaque TTO-55 (A)" from Ishihara, and "UVT 14/4" from Kemira; with alumina and with aluminum stearate, such as the product "Microtitanium Dioxide MT 100 T, MT 100 TX, MT 100 Z or MT-01" from Tayca, the products "Solaveil CT-10 W" and "Solaveil CT 100" from Uniqema, and the product "Eusolex T-AVO" from Merck; with alumina and with aluminum laurate, such as the product "Microtitanium Dioxide MT 100 S" from Tayca; with iron oxide and with iron stearate, such as the product "Microtitanium Dioxide MT 100 F" from Tayca; with zinc oxide and with zinc stearate, such as the product "BR351" from Tayca; with silica and with alumina and treated with a silicone, such as the products "Microtitanium Dioxide MT 600 SAS", "Microtitanium Dioxide MT 500 SAS", and "Microtitanium Dioxide MT 100 SAS" from Tayca; with silica, with alumina and with aluminum stearate and treated with a silicone, such as the product "STT-30-DS" from Titan Kogyo; with silica and treated with a silicone, such as the product "UV-Titan X 195" from Kemira; with alumina and treated with a silicone, such as the products "Tipaque TTO-55 (S)" from Ishihara or "UV Titan M 262" from Kemira; with triethanolamine, such as the product "STT-65-S" from Titan Kogyo; with stearic acid, such as the product "Tipaque TTO-55 (C)" from Ishihara; or with sodium hexametaphosphate, such as the product "Microtitanium Dioxide MT 150 W" from Tayca. Other titanium oxide pigments treated with a silicone are, and in some embodiments $TiO_2$ treated with octyltrimethylsilane and for which the mean size of the individual particles is from 25 and 40 nm, such as that marketed under the trademark "T 805" by Degussa Silices, $TiO_2$ treated with a polydimethylsiloxane and for which the mean size of the individual particles is 21 nm, such as that marketed under the trademark "70250 Cardre UF TiO2Si3" by Cardre, and anatase/rutile $TiO_2$ treated with a polydimethylhydrosiloxane and for which the mean size of the individual particles is 25 nm, such as that marketed under the trademark "Microtitanium Dioxide USP Grade Hydrophobic" by Color Techniques.

And in some embodiments, the following coated $TiO_2$ can be used as the coated inorganic UV filter: Stearic acid (and) Aluminum Hydroxide (and) $TiO_2$, such as the product "MT-100 TV" from Tayca, with a mean primary particle diameter of 15 nm; Dimethicone (and) Stearic Acid (and) Aluminum Hydroxide (and) $TiO_2$, such as the product "S A-TTO-S4" from Miyoshi Kasei, with a mean primary particle diameter of 15 nm; Silica (and) $TiO_2$, such as the product "MT-100 WP" from Tayca, with a mean primary particle diameter of 15 nm; Dimethicone (and) Silica (and) Aluminum Hydroxide (and) $TiO_2$, such as the product "MT-Y02" and "MT-Y-110 M3S" from Tayca, with a mean primary particle diameter of 10 nm; Dimethicone (and) Aluminum Hydroxide (and) $TiO_2$, such as the product "SA-TTO-S3" from Miyoshi Kasei, with a mean primary particle diameter of 15 nm; Dimethicone (and) Alumina (and) $TiO_2$, such as the product "UV TITAN MI 70" from Sachtleben, with a mean primary particle diameter of 15 nm;. and Silica (and) Aluminum Hydroxide (and) Alginic Acid (and) $TiO_2$, such as the product "MT-100 AQ" from Tayca, with a mean primary particle diameter of 15 nm. In terms of UV filtering ability, $TiO_2$ coated with one or a combination of organic UV filter is more desirable. For example, Avobenzone (and) Stearic Acid (and) Aluminum Hydroxide (and) $TiO_2$, such as the product "HXMT-100ZA" from Tayca, with a mean primary particle diameter of 15 nm, can be used.

The uncoated titanium oxide pigments are, for example, marketed by Tayca under the trademarks "Microtitanium Dioxide MT500B" or "Microtitanium Dioxide MT600B", by Degussa under the trademark "P 25", by Wacker under the trademark "Oxyde de titane transparent PW", by Miyoshi Kasei under the trademark "UFTR", by Tomen under the trademark "ITS" and by Tioxide under the trademark "Tioveil AQ". The uncoated zinc oxide pigments are, for example: those marketed under the trademark "Z-cote" by Sunsmart; those marketed under the trademark "Nanox" by Elementis; and those marketed under the trademark "Nanogard WCD 2025" by Nanophase Technologies. The coated zinc oxide pigments are, for example: those marketed under the trademark "Oxide Zinc CS-5" by Toshiba (ZnO coated with polymethylhydrosiloxane); those marketed under the trademark "Nanogard Zinc Oxide FN" by Nanophase Technologies (as a 40% dispersion in Finsolv TN, C12-C15 alkyl benzoate); those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nano-oxides coated with silica and polymethylhydrosiloxane); those marketed under the trademark "NFD Ultrafine ZnO" by Daikin (ZnO coated with phosphate of perfluoroalkyl and a copolymer based on perfluoroalkylethyl as a dispersion in cyclopentasiloxane); those marketed under the trademark "SPD-Z1" by Shin-Etsu (ZnO coated with a silicone-grafted acrylic polymer dispersed in cyclodimethylsiloxane); those marketed under the trademark "Escalol Z100" by ISP (alumina-treated ZnO dispersed in an ethylhexyl methoxycinnamate/PVP-hexadecene copolymer/methicone mixture); those marketed under the trademark "Fuji ZnO-SMS-10" by Fuji Pigment (ZnO coated with silica and polymethylsilsesquioxane); and those marketed under the trademark "Nanox Gel TN" by Elementis (ZnO dispersed at 55% in C12-C15 alkyl benzoate with hydroxystearic acid polycondensate). The uncoated cerium oxide pigments are marketed, for example, under the trademark "Colloidal Cerium Oxide" by Rhone-Poulenc.

The uncoated iron oxide pigments are, for example, marketed by Arnaud under the trademarks "Nanogard WCD 2002 (FE 45B)", "Nanogard Iron FE 45 BL AQ", "Nanogard FE 45R AQ", and "Nanogard WCD 2006 (FE 45R)", or by Mitsubishi under the trademark "TY-220". The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345", and "Nanogard FE 45 BL", or by BASF under the trademark "Oxyde de fer transparent".

Optional Organic UV Filters

In some embodiments, the sunscreen composition may include one or a combination of organic UV filters. The organic UV filters may be active in the UV-A and/or UV-B region. The organic UV filter may be hydrophilic and/or lipophilic. The organic UV filter may be solid or liquid. The terms "solid" and "liquid" mean solid and liquid, respectively, at 25° C. under 1 atm.

The organic UV filter can be selected from the group consisting of anthranilic compounds; dibenzoylmethane compounds; cinnamic compounds; salicylic compounds; camphor compounds; benzophenone compounds; ÿ,ÿ-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis(hydroxyphenylbenzotriazole) compounds; benzoxazole compounds; screening polymers and screening silicones; dimers derived from a-alkylstyrene; 4,4-diarylbutadienes compounds; guaiazulene and derivatives thereof; rutin and derivatives thereof; flavonoids; bioflavonoids; oryzanol and derivatives thereof; quinic acid and derivatives thereof; phenols; retinol; cysteine; aromatic amino acids; peptides having an aromatic amino acid residue; and mixtures thereof.

Mention may be made, as examples of the organic UV filter(s), of those denoted below under their INCI names, and mixtures thereof. Anthranilic compounds: Menthyl anthranilate, marketed under the trademark "Neo Heliopan MA" by Haarmann and Reimer. Dibenzoylmethane compounds: Butyl methoxydibenzoylmethane, marketed, in particular, under the trademark "Parsol 1789" by Hoffmann-La Roche; and isopropyl dibenzoylmethane. Cinnamic compounds: Ethylhexyl methoxycinnamate, marketed, in particular, under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate. Salicylic compounds: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer. Camphor compounds, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; terephthalylidene dicamphor sulfonic acid, manufactured under the trademark "Mexoryl SX" by Chimex; and polyacrylamidomethyl benzylidene camphor, manufactured under the trademark "Mexoryl SW" by Chimex. Benzophenone compounds: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxybenzophenone) or oxybenzone, marketed under the trademark "Uvinul M40" by BASF; benzophenone-4 (hydroxymethoxy benzophenone sulfonic acid), marketed under the trademark "Uvinul MS40" by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; and benzophenone-12, and n-hexyl 2-(4-diethylamino-2-hydroxybenzoyl)benzoate (UVINUL A+by BASF). ÿ,ÿ-Diphenylacrylate compounds: Octocrylene, marketed in particular under the trademark "Uvinul N539" by BASF; and Etocrylene, marketed in particular under the trademark "Uvinul N35" by BASF. Triazine compounds: Diethylhexyl butamido triazone, marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine marketed under the trademark «TINOSORB S» by CIBA GEIGY, and ethylhexyl triazone marketed under the trademark «UVTNUL T150» by BASF. Benzotriazole compounds, in particular, phenylbenzotriazole derivatives: 2-(2H-benzotriazole-2-yl)-6-dodecyl-4-methylpheno, branched and linear; and those described in U.S. Pat. No. 5,240,975. Benzalmalonate compounds: Dineopentyl 4'-methoxybenzalmalonate, and polyorganosiloxane comprising benzalmalonate functional groups, such as poly-silicone-15, marketed under the trademark "Parsol SLX" by Hoffmann-LaRoche. Benzimidazole compounds, in particular, phenylbenzimidazole derivatives: Phenylbenzimidazole sulfonic acid, marketed in particular under the trademark "Eusolex 232" by Merck, and disodium phenyl dibenzimidazole tetrasulfonate, marketed under the trademark "Neo Heliopan AP" by Haarmann and Reimer. Imidazoline compounds: Ethylhexyl dimethoxybenzylidene dioxoimidazoline propionate. Bis-benzoazolyl compounds: The derivatives as described in EP-669,323 and U.S. Pat. No. 2,463,264. Para-aminobenzoic acid compounds: PABA (p-aminobenzoic acid), ethyl PABA, Ethyl dihydroxypropyl PABA, pentyl dimethyl PABA, ethylhexyl dimethyl PABA, marketed, in particular, under the trademark "Escalol 507" by ISP, glyceryl PABA, and PEG-25 PABA, marketed under the trademark "Uvinul P25" by BASF. Methylene bis-(hydroxyphenylbenzotriazol) compounds, such as 2,2'-methylenebis [6-(2H-benzotriazol-2-yl)-4-methyl-phenol] marketed in the solid form under the trademark "Mixxim BB/200" by Fairmount Chemical, 2,21-methylenebis [6-(2H-benzotriazol-2-yl)-4-(1,1,3,3-tetramethylbutyl) phenol] marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071 and 5,166,355, GB-2,303,549, DE-197,26,184, and EP-893,119, and Drometrizole trisiloxane, marketed under the trademark "Silatrizole" by Rhodia Chimie or-"Mexoryl XL" L'Oreal. by Benzoxazole compounds: 2,4-bis [5-I (dimethylpropyl) benzoxazol-2-yl-(4-phenyl) imino]-6-(2-ethylhexyl) imino-1,3,5-triazine, marketed under the trademark of Uvasorb K2A by Sigma 3V. Screening polymers and screening silicones: The silicones described in WO 93/04665. Dimers derived from a-alkylstyrene: The dimers described in DE-19855649. 4,4-Diarylbutadiene compounds: I,I-dicarboxy (2,2'-dimethylpropyl)-4,4-diphenylbutadiene.

In some embodiments the organic UV filter(s) may be selected from the group consisting of: butyl methoxydibenzoylmethane, ethylhexyl methoxycinnamate, homosalate, ethylhexyl salicylate, phenylbenzimidazole sulfonic acid, benzophenone-3, benzophenone-4, benzophenone-5, n-hexyl 2-(4-diethylamino-2-hydroxybenzoyl)benzoate, I,r-(1,4-piperazinediyl) bis [I-[2-[4-(diethylamino)-2-hydroxy-benzoyl] phenyl]-methanone 4-methylbenzylidene camphor, terephthalylidene dicamphor sulfonic acid, disodium phenyl dibenzimidazole tetrasulfonate, ethylhexyl triazone, bis-ethylhexyloxyphenol methoxyphenyl triazine, diethylhexyl butamido triazone, 2,4,6-tris(dineopentyl 4'-amino-benzalmalonate)-s-triazine, 2,4,6-tris(diisobutyl 4'-amino-benzalmalonate)-s-triazine, 2,4-bis-(n-butyl 4'-aminobenzalmalonate)-6-[(3-{1,3,3,3-tetramethyl-1-[(trimethylsilyloxy]-disiloxanyl}propyl) amino]-s-triazine, 2,4,6-tris-(di-phenyl)-triazine, 2,4,6-tris-(ter-phenyl)-triazine, methylene bis-benzotriazolyl tetramethylbutylphenol, drometrizole trisiloxane, polysilicone-15, dineopentyl 4'-methoxybenzalmalonate, I,l-dicarboxy (2,2'-dimethylpropyl)-4,4-diphenylbutadiene, 2,4-bis [5-1 (dimethylpropyl) benzoxazol-2-yl-(4-phenyl) imino]-6-(2-ethylhexyl) imino-1,3,5-triazine, camphor benzylkonium methosulfate, and mixtures thereof.

Water

In accordance with the various embodiments, the sunscreen composition includes water.

In various embodiments, the sunscreen composition comprises from about 40% to about 75% water, and in some embodiments from about 45% to about 60% water, including increments and all ranges and subranges therein and there between, by weight, based on the total weight of the sunscreen composition. One of ordinary skill in the art, however, will appreciate that other ranges are within the scope of the invention. Thus, water is present, by weight, based on the total weight of the sunscreen composition, from about 40, 45, 50, 55, 60, 65, 66, 67, 68, 69, 70, 71, 72, 73, 74, to about 75 weight percent, including increments and all ranges and subranges therein and there between.

The water used in the sunscreen composition may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-bains, water from Saint Gervais-les-Bains, water from Neris-les-Bains, water from Allevar-les-Bains, water from Digne, water from Maizieres, water from Neyrac-les-Bains, water from Lons-le-saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

Other Ingredients

In accordance with various embodiments, the sunscreen composition according to the disclosure includes one or more ingredients that may include one or more solvents in one or both of the aqueous phase and the oil phase of the emulsion.

In some embodiments, the sunscreen composition includes ingredients selected from the group consisting of water based solvents such as glycols, SPF boosters and stabilizers, oil based solvents, oils, and waxes (as further described below), and combinations thereof. In some embodiments, the sunscreen composition includes solvents selected from the group consisting of glycerin, propanediol, ethylhexyl methoxycrylene, butyloctyl salicylate, coco-caprylate/caprate, dicaprylyl carbonate, dicaprylyl ether, isopropyl palmitate, and combinations thereof.

In the various embodiments, solvents can be present from about 0.1% to about 50%, or from about 0.5% to about 45%, or from about 1% to about 20%, or from about 1% to about 10%, or from about 1% to about 5%, or from about 2% to about 15%, or from about 3% to about 12%, or from about 4% to about 10%, or any suitable combination, sub-combination, range, or sub-range thereof by weight, based on the total weight of the sunscreen composition. One of ordinary skill in the art, however, will appreciate that other ranges are within the scope of the invention.

In some particular embodiments, the solvents can include one or a mix of glycols, for example glycerin and propanediol, present in combination from about 5% to about 15%, one or a mix of SPF boosters and stabilizers, for example ethylhexyl methoxycrylene and butyloctyl salicylate, present in combination from about 2% to about 10%, and one or a mix of oils, for example coco-caprylate/caprate present from about 3% to about 10%.

Thus, any one solvent or combination of solvents may be present, by weight, based on the total weight of the sunscreen composition, is from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, to about 50 weight percent, including increments and ranges therein and there between.

SPF Boosters

In accordance with some embodiments, the sunscreen composition according to the disclosure may comprise one or a combination of SPF boosters.

In some embodiments, the SPF booster is selected from Butyloctyl Salicylate, ethylhexyl methoxycrylene, styrene/acrylates copolymer (such as the product sold under the tradename SUNSPHERES™), Ethylenediamine/Stearyl Dimer Dilinoleate Copolymer, Dimethicone and Acrylates/Dimethicone Copolymer, silicone polymer comprising dimethicone (and) dimethicone/vinyl dimethicone copolymer, the UVA booster Solastay, and combinations thereof. In some particular embodiments, the SPF booster comprises one or more of Butyloctyl Salicylate and styrene/acrylates copolymer.

The one or combination of SPF boosters, when present, may be at a concentration from about 0.01% to 25%, in some embodiments from about 0.1% to 13%, and in some embodiments from about 0.5% to 10, and in some embodiments from about 1% to 5% by weight, all weights based on the total weight of the sunscreen composition. Thus, in various embodiments, an SPF booster, when present, may be present in a composition in a weight percent amount from 0.01, 0.02, 0.03, 0.04, 0.05, 0.06, 0.07, 0.08, 0.09, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0 to 25.0 percent by weight, including increments there between.

Cosmetic Oils/Emollients

In accordance with the various embodiments, the sunscreen composition may include any one or a combination of cosmetic oils. In some embodiments, the oil is generally immiscible in water. The oil may be selected from hydrocarbons, silicones, fatty alcohols, glycols, and vegetable oils. The oil may include one or a combination of polar and non-polar oil. In some embodiments, the oil may be chosen from hydrocarbon-based oils from plants or of plant origin, mineral oil, ester oils, fatty alcohols containing from 12 to 26 carbon atoms, fatty acids containing from 12 to 26 carbon atoms and vinylpyrrolidone copolymers, and combinations thereof.

In some particular embodiments, the oil may be selected from the group consisting of, coco-caprylate/caprate, dicaprylyl carbonate, dicaprylyl ether, isopropyl palmitate, and combinations thereof.

The term "silicone oil" relates to oil comprising at least one silicon atom, and especially at least one Si—O group. The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil, or a synthetic hydrocarbon-based oil. Further, suitable oil may be a mineral hydrocarbon-based oil, a plant hydrocarbon-based oil, or a synthetic hydrocarbon-based oil.

Silicone Oils

The sunscreen composition may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the sunscreen composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy) diphenylsiloxanes, diphenyl dimethicones, diphenyl(methyldiphenyl) trisiloxanes or (2-phenylethyl)trimethylsiloxysilicates.

Other examples of silicone oils that may be mentioned include volatile linear or cyclic silicone oils, especially those with a viscosity 8 centistokes ($8\times10^6$ $m^2/s$) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, dodecamethylpentasiloxane, and mixtures thereof. decamethyltetrasiloxane and Fluoro Oils The sunscreen composition may comprise one or more fluoro oils. For example, the one or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The sunscreen composition may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the sunscreen composition may include a synthetic oil selected from the group consisting of hydrogenated polyisobutene and hydrogenated polydecene. A hydrocarbon-based oil may be a non-volatile hydrocarbon-based, such as:

(i) hydrocarbon-based oils of plant origin, such as glyceride triesters, which are generally triesters of fatty acids and of glycerol, the fatty acids of which can have varied chain lengths from C4 to C24, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is y 10, for instance Purcellin oil (cetearyl octanoate), isopropyl myristate, isopropyl palmitate, C12-C15 alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear C12-C13 alkyl) tartrates, such as those sold under the name Cosmacol ETI® by Enichem Augusta Industriale, and also di(linear C14-C15 alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid, or linolenic acid;

(vii) carbonates, such as dicaprylyl carbonate, such as the product sold under the name Cetiol CC (TM) by Cognis;

(viii) fatty amides, such as isopropyl N-lauroyl sarcosinate, such as the product sold under the trade name Eldew SL 205 (TM) from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

Hydrocarbon-based oils may be glyceride triesters and in particular to caprylic/capric acid triglycerides, synthetic esters and in particular isononyl isononanoate, oleyl erucate, C12-C15 alkyl benzoate, 2-ethylphenyl benzoate and fatty alcohols, such as octyldodecanol. As volatile hydrocarbon-based oils, mention is made of hydrocarbon-based oils containing from 8 to 16 carbon atoms and in particular of branched C8-C16 alkanes, such as C8-C16 isoalkanes of petroleum origin (also known as isoparaffins), such as isododecane (also known as 2,2,4,4,6-pentamethylheptane), isodecane or isohexadecane, the oils sold under the Isopar or Permethyl trade names, branched C C8-C16 esters, and isohexyl neopentanoate.

In some embodiments, the sunscreen composition may comprise one or more oils such as from those described herein above, and from oils that may be selected from branched or linear, liquid alkane with carbon chain length of C11 to C20. In various embodiments, liquid alkanes may be selected from those with a carbon chain length of from C11 to C20. The liquid alkanes may be selected from those with a carbon chain length of from C11 to C20, or from C15 to C19, or one of C11, C12, C13, C14, C15, C16, C17, C18 to C19. In some embodiments, suitable liquid alkanes that may be used according to the disclosure include hydrocarbon-based oils containing from 8 to 16 carbon atoms, and especially branched C8-C16 alkanes such as C8-C16 isoalkanes.

In some embodiments, the sunscreen composition may comprise one or more oils selected from polar emollients selected from esters, triglycerides, ethers, carbonates, alcohols, oils, butters, fatty acids, and their combinations thereof. In various embodiments, the polar emollients may be selected from those with a molecular weight of 400 g/mol or less. More, generally, the polar emollient may have a molecular weight in the range from about 50 g/mol % to about 350 g/mol.

In some embodiments, the sunscreen composition may comprise polar emollients that include those derived from C12-C50 fatty acids, preferably C16-C22 saturated fatty acids, and monohydric alcohols. In some embodiments, such esters may be chosen from isopropyl myristate, methyl palmitate, isopropyl laurate, isopropyl palmitate, ethylhexyl palmitate, ethylhexyl laurate, ethylhexyl oleate, ethylhexyl isononanoate, myristyl myristate, 2-ethylhexyl caprate/caprylate (or octyl caprate/caprylate), 2-ethylhexyl palmitate, isostearyl neopentanoate, isononyl isononanoate, hexyl laurate, esters of lactic acid and of fatty alcohols comprising 12 or 13 carbon atoms, dicaprylyl carbonate and their mixtures.

The one or more oil, when present, alone or in combination as a blend of oils, may be present in the sunscreen composition from about 0.0001% to about 20% or from about 0.001% to about 0.0010%, or from about 0.003% to about 0.004%, or from about 0.01% to about 0.1%, or from about 0.1% to about 10%, or from about 0.5% to about 20%, or from about 1% to about 10%, or from about 5% to about 10%, or from about 2% to about 7%, or from about 0.5% to about 2%, or from about 0.008% to about 0.01%, or from about 0.1% to about 0.2%, or from about 0.5% to about 2%, or from about or any suitable combination, sub-combination, range, or sub-range thereof by weight, based on the weight of the sunscreen composition. One of ordinary skill in the art, however, will appreciate that other ranges are within the scope of the invention. In some embodiments, the sunscreen composition includes more than one oil, each oil present in an amount as set forth herein above, wherein each different oil (such as, for example, plant oils and extracts with oils) may be present within one of the ranges selected from the ranges set forth herein above.

Thus, each of the at least one oil or combination of oils is present by weight, based on the total weight of the sunscreen composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19 to about 20 percent, including increments and ranges therein and there between.

Cosmetic Waxes

In accordance with the disclosure, optionally one or more wax may be present in the sunscreen composition, the wax selected from natural and synthetic waxes. Natural waxes can include animal tallow, bayberry wax, beeswax, grapefruit wax, orange peel wax, palm wax, rice bran wax, sumac wax, sunflower wax, soy wax, polyhydroxystearic acid, and combinations thereof.

In some embodiments, when present, a wax may be selected from Oryza sativa cera (rice bran wax), candelilla wax, sunflower seed wax, carnauba wax, polyhydroxystearic acid, and combinations thereof. In a particular embodiment, the composition comprises rice bran wax.

In accordance with the various embodiments, the one or wax, when present, is present in the composition at a concentration, by weight, of between about 0.1% to about 10%, or from about 0.2% to about 4%, or from about 0.5% to about 3%, or from about 1% to about 2%, or any suitable combination, sub-combination, range, or sub-range thereof by weight, based on the weight of the sunscreen composition.

In some embodiments, the composition comprises a more than one wax, each one present in the composition at a concentration, by weight, based on the total weight of sunscreen composition, in the range from about 0.1% to about 10%, or any suitable combination, sub-combination, range, or sub-range thereof by weight, based on the weight of the sunscreen composition.

Thus, when present, the wax is present by weight, based on the total weight of the sunscreen composition from about 0.10, 0.20, 0.30, 0.40, 0.50, 0.60, 0.70, 0.80, 0.90, 1.0, 2, 3, 4, 5, 6, 7, 8, 9, to about 10 weight percent, including increments and ranges therein and there between.

Powders

In accordance with some embodiments, the sunscreen composition according to the disclosure may optionally comprise one or a combination of powders comprising sensorial feel modifying powders. In some particular embodiments, the powders may be selected from boron nitride, perlite, and aluminium starch octenyl succinate.

The one or combination of powders, when present, may be at a concentration from about 0.05% to 15%, in some embodiments from about 0.1% to 10%, and in some embodiments from about 1% to 5% by weight, all weights based on the total weight of the sunscreen composition. Thus, in various embodiments, a powder, when present, may be present in a composition in a weight percent amount from 0.05, 0.06, 0.07, 0.08, 0.09, 1.0, 2.0, 3.0, 4.0, 5.0, 6.0, 7.0, 8.0, 9.0, 10.0, 11.0, 12.0, 13.0, 14.0, to 15.0 percent by weight, including increments there between.

Hydrating Agents

In accordance with the disclosure, in some embodiments, one or a combination hydrating agents or humectants may be present in the sunscreen composition. The hydrating agent present in the cosmetic composition, according to the disclosure, includes, but is not limited to, one or a combination of polyols, including, for example, glycerin, glycerol, glycols, such as caprylyl glycol, butylene glycol, propanediol, propylene glycol, isoprene glycol, dipropylene glycol, hexylene glycol and polyethylene glycols, monoethylene glycol, diethylene glycol, triethylene glycol, diethylene glycol, hexylene glycol, glycol ethers such as monopropylene, dipropylene and tripropylene glycol alkyl($C_1$-$C_4$) ethers, squalane, triacetin, sugars, such as glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In some embodiments, the sunscreen composition includes a hydrating agent selected from one or a combination of glycerin present at about 7% and propanediol present at about 1%.

In accordance with the various embodiments, the amount of hydrating agent present in the sunscreen composition can range from about 1% to about 25%, or from about 2% to about 20%, or from about 3% to about 5% or any suitable combination, sub-combination, range, or sub-range thereof by weight, based on the total weight of the sunscreen composition. One of ordinary skill in the art, however, will appreciate that other ranges are within the scope of the invention.

Thus, any one of or a combination of hydrating agent may be present, by weight, based on the total weight of the sunscreen composition, is from about 1, 2, 3, 4, 5, 6, 7, 8, 9, 10, 11, 12, 13, 14, 15, 16, 17, 18, 19, 20, 21, 22, 23, 24, to about 25 weight percent, including increments and ranges therein and there between.

Actives/Optional Additives

The sunscreen compositions can also comprise one or a combination of actives or optional additives used in the cosmetics field which does not affect the properties of the sunscreen compositions according to the invention, such as fragrances, dyes, pearlescent agents, silica, preservatives, proteins, protein hydrolysates, sodium hyaluronate, vitamins, panthenol, silicones, odor absorbers and coloring materials; anti-microbial components, including, but not limited to, phenoxyethanol, chlorphenesin, capryloyl glycol and sodium salicylate; essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang; fruit extracts, for example Pyrus Malus (Apple) Fruit Extract, and Aloe Barbadensis Leaf Juice Powder; citric acid, sodium chloride; neutralizing or pH-adjusting agents (e.g., triethylamine (TEA) and sodium hydroxide), and combinations thereof.

Although the actives/optional additives are given as examples, it will be appreciated that other optional components compatible with cosmetic applications known in the art may be used.

In some particular embodiments, the sunscreen composition may include comprising one or a combination of diethylhexyl syringylidenemalonate, trisodium ethylenediamine disuccinate, hydroxyacetophenone, citric acid, chlorphenesin, EDTA, Sodium Hyaluronate, panthenol, tocopherol, niacinamide, Disodium Magnesium Sulfate and combinations thereof.

In some particular embodiments, the sunscreen composition may include actives comprising one or a combination of thickeners selected from hydroxyethyl acrylate/sodium acryloyldimethyl taurate copolymer, polyhydroxystearic acid (wax), xanthan gum, or a combination thereof. In some particular embodiments, the sunscreen composition may include antimicrobials comprising phenoxyethanol.

In accordance with the various embodiments, the amount of each one or a combination of actives/optional additives, when present in the sunscreen composition can be present in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the sunscreen composition. And in some embodiments, a combination of actives present in the sunscreen composition can be present in a range from about 0.001% to about 20%.

Thus, any one or a combination of actives/optional additives, when present, may be present, by weight, based on the total weight of the sunscreen composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

The instant disclosure also relates to methods for protecting skin from UV radiation comprising applying an effective amount of the sunscreen composition of claim 1 to the skin.

EXAMPLES

The following Examples are provided for illustrative purposes only and are not intended to be limiting.

EXAMPLE 1: Raw Materials

Selected raw materials as used in the sunscreen composition are identified in the table below.

TABLE 1

| Representative Raw Materials | | |
|---|---|---|
| Raw Material | Source | Percent Active |
| *C12-22 ALKYL ACRYLATE/ HYDROXYETHYLACRYLATE COPOLYMER | Intelimer (TM) H4, from Air Products | 100% |
| ZINC OXIDE (and) TRIETHOXYCAPRYLYLSILANE | | ~98% |
| TITANIUM DIOXIDE | | ~82% |
| STEARETH-20 | | 100% |
| STEARETH-2 | | 100% |
| LAURETH-23 | | 100% |

*Example of lipophilic acrylate-based oil thickener Intelimer (TM), Poly C10-30 poly-acrylate.

EXAMPLE 2: Inventive and Base Compositions

A plant-scalable sunscreen composition according to the disclosure was prepared and which has demonstrated physical and chemical properties as described herein below. The inventive composition was evaluated by an FDA Method in vivo SPF characterization, achieving a value of 50 or higher, as described herein below.

TABLE 2

| Inventive Example | |
|---|---|
| INGREDIENT | INVENTIVE COMPOSITION |
| STEARETH-2 and STEARETH-20 | ~2 |
| ACTIVES (DIETHYLHEXYL SYRINGYLIDENEMALONATE, TRISODIUM ETHYLENEDIAMINE DISUCCINATE, HYDROXYACETOPHENONE, CITRIC ACID) | ~1.4 |
| EMOLLIENT (COCO-CAPRYLATE/CAPRATE) | ~5 |
| WAX (ORYZA SATIVA CERA AND POLYHYDROXYSTEARIC ACID) | ~1.5 |
| XANTHAN GUM | 0.2 |

TABLE 2-continued

| Inventive Example | |
|---|---|
| INGREDIENT | INVENTIVE COMPOSITION |
| HYDROXYETHYL ACRYLATE/SODIUM ACRYLOYLDIMETHYL TAURATE COPOLYMER | 0.3 |
| C12-22 ALKYL ACRYLATE/ HYDROXYETHYLACRYLATE COPOLYMER | 1.5 |
| PRESERVATIVE (CHLORPHENESIN) | ~0.2 |
| AQUA | ~48 |
| GLYCERIN AND PROPANEDIOL | ~10 |
| ZINC OXIDE (and) TRIETHOXYCAPRYLYLSILANE | ~] |
| ORGANIC UV AGENTS, AND SPF BOOSTERS (~4%) (ETHYLHEXYL METHOXYCRYLENE, BUTYLOCTYL SALICYLATE, ETHYLHEXYL SALICYLATE (OCTYL SALICYLATE), OCTOCRYLENE, HOMOSALATE) | ~22 |

Poly C10-30 poly acrylate: Intelimer (TM) products from the company Air Products.

TABLE 3

| Base Composition | |
|---|---|
| INGREDIENT | BASE |
| ACTIVES (DIETHYLHEXYL SYRINGYLIDENEMALONATE, TRISODIUM ETHYLENEDIAMINE DISUCCINATE, HYDROXYACETOPHENONE, CITRIC ACID) | ~1.4 |
| EMOLLIENT (COCO-CAPRYLATE/CAPRATE) | ~5 |
| WAX (ORYZA SATIVA CERA AND POLYHYDROXYSTEARIC ACID) | ~1.5 |
| XANTHAN GUM | 0.2 |
| HYDROXYETHYL ACRYLATE/SODIUM ACRYLOYLDIMETHYL TAURATE COPOLYMER | 0.3 |
| C12-22 ALKYL ACRYLATE/ HYDROXYETHYLACRYLATE COPOLYMER | 1.5 |
| CHLORPHENESIN | 0.2 |
| AQUA | ~48 |
| GLYCERIN AND PROPANEDIOL | ~10 |
| SPF BOOSTERS (ETHYLHEXYL METHOXYCRYLENE AND BUTYLOCTYL SALICYLATE) | ~4 |

The foregoing Base composition was used to provide each of Comparative Compositions #1, #2 and #3, wherein:

Comparative #1 further included:
ethylhexyl salicylate (octyl salicylate), 5%
octocrylene sun filter, 5%
homosalate sun filter, 8%
Comparative #2 further included:
ethylhexyl salicylate (octyl salicylate), 5%
octocrylene sun filter, 5%
homosalate sun filter, 8%
zinc oxide (and) triethoxycaprylylsilane, ~7%
Comparative #3 further included:
ethylhexyl salicylate (octyl salicylate), 5%
octocrylene sun filter, 5%
homosalate sun filter, 8%
zinc oxide (and) triethoxycaprylylsilane, ~7%
glyceryl stearate citrate, 1%

EXAMPLE 3: Emulsion structural stability and Processibility Testing of Inventive and Comparative Compositions A panel of compositions were tested for SPF and emulsion structural stability and processability. The results are shown in Table 3, below.

TABLE 3

| Feature | Comparative #1 (Base + Organic UV filters) | Comparative #2 (Base + ZnO + Organic UV filters) | Comparative #3 (Base + ZnO + Organic UV filters anionic emulsifier) | Inventive Composition #1 |
|---|---|---|---|---|
| Stability | YES | YES | NO | YES |
| Processibility | YES | NO | NO | YES |
| SPF 50 in vivo test | YES | NO | NO | YES |

According to the data collected for the inventive and comparative examples, it is apparent that the base composition with only organic UV filters provides stability, processability and demonstrates a high SPF, but, upon addition of ZnO the processability and SPF were lost. Further, upon addition of an anionic emulsifier the stability was also lost. The inventive composition demonstrates that both inorganic and organic UV filters can be present in an amount that is about 25% of the sunscreen composition, by weight, to provide a high SPF composition that demonstrates long term stability (12 weeks) and permits scaled processing.

EXAMPLE 4: Emulsion structural stability and Processibility Testing of Inventive and Comparative Compositions An inventive and a comparative composition were tested using only inorganic UV filters (no organic UV actives). The inventive formula was prepared using C12-15 Alkyl Acrylate/Hydroxyethylacrylate copolymer and the comparative formula was prepared without the polymer and with an increased concentration of emulsifiers. The results are shown in Table 4, below.

TABLE 4

| INGREDIENTS | INVENTIVE EXAMPLE | COMPARATIVE EXAMPLE |
|---|---|---|
| WATER | QS | QS |
| THICKENER | 1.9 | 1.9 |
| EMOLLIENT | 16 | 16 |
| SILICONE | 3.5 | 3.5 |
| STEARETH-20 and STEARETH-2 | ~1 | ~2.4 and 0.9 |
| BEHENYL ALCOHOL | 0.25 | 0.25 |
| GLYCERYL STEARATE | 0 | 0.5 |
| SPF BOOSTERS | 4 | 4 |
| PRESERVATIVE | 1 | 1 |
| DISPERSING AGENT | 0.65 | 0.65 |
| TITANIUM DIOXIDE | 5.12 | 10 |
| ZINC OXIDE | 16.41 | 12.5 |
| VITAMIN E | 3 | 3 |
| C12-15 ALKYL ACRYLATE/ HYDROXYETHYLACRYLATE COPOLYMMER | 1 | 0 |
| Physical Stability | Stable | Unstable |

The comparison demonstrates that independent of the presence of organic UV filters, the sunscreen composition according to the invention provides a high SPF composition that demonstrates long term stability (12 weeks) and permits scaled processing.

While the disclosure has been described with reference to a preferred embodiment, it will be understood by those skilled in the art that various changes may be made, and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure is not limited to the particular embodiment disclosed as the best mode contemplated for carrying out this disclosure, but that the disclosure will include all embodiments falling within the scope of the appended claims.

The compositions and methods of the present disclosure can comprise, consist of, or consist essentially of the essential elements and limitations of the disclosure described herein, as well as any additional or optional ingredients, components, or limitations described herein or otherwise useful. The terms "comprising," "having," and "including" are used in their open, non-limiting sense. The expression "inclusive" for a range of concentrations means that the limits of the range are included in the defined interval.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present disclosure, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

As used herein, the expression "at least one" is interchangeable with the expression "one or more" and thus includes individual components as well as mixtures/combinations. The terms "a" and "the" are understood to encompass the plural as well as the singular.

The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The phrase "viscosity" refers to the thickness of a fluid or composition and is a measurement of a fluid or composition's resistance to flow. Herein, "viscosity" is synonymous to "dynamic viscosity" or "absolute viscosity", rather than "kinematic viscosity", and is measured by means of a rheometer in a method which is known to those skilled-in-the-art. Measurements of viscosity herein are reported in pascal-seconds (Pas) unless otherwise specified.

The term "INCI" is an abbreviation of International Nomenclature of Cosmetic Ingredients, which is a system of names provided by the International Nomenclature Committee of the Personal Care Products Council to describe personal care ingredients.

The term "weight ratio" or "mass ratio" as used herein, references the amount of a substance in proportion to a mixture containing said substance, and is calculated by dividing the amount of said substance by weight contained in the mixture by the weight of the mixture containing said substance. As an example, a weight ratio of 0.4 for substance A in a mixture of A, B, and C indicates that the weight of substance A divided by the total weight of substances A, B, and C is 0.4.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A sunscreen composition comprising an oil-in-water emulsion of aqueous and oil phases, comprising:
   i. at least one lipophilic oil thickener comprising C12-22 alkyl acrylate/hydroxyethylacrylate copolymer;
   ii. at least one mineral UV filter including zinc oxide; and
   iii. at least one nonionic surfactant selected from the group consisting of polyethylene glycol ethers, polyethylene glycol esters of fatty acids, and combinations thereof,
   wherein the composition has an SPF in a range from about 30 to about 55 and exhibits phase stability and processibility.

2. The sunscreen composition according to claim 1, wherein:
   i. the C12-22 alkyl acrylate/hydroxyethylacrylate copolymer is present from about 0.5% to about 5%;
   ii. the zinc oxide is present from about 1% to about 25%; and
   iii. the at least one nonionic surfactant selected from the group consisting of polyethylene glycol ethers, polyethylene glycol esters of fatty acids, and combinations thereof is present from at least about 0.1% to about 5%,
   wherein the components are present by weight, based on the total weight of the sunscreen composition.

3. The sunscreen composition according to claim 1, wherein:
   i. the C12-22 alkyl acrylate/hydroxyethylacrylate copolymer is present from about 0.75% to about 3%;
   ii. the zinc oxide is present from about 5% to about 15%; and
   iii. the at least one nonionic surfactant selected from the group consisting of polyethylene glycol ethers, polyethylene glycol esters of fatty acids, and combinations thereof is present from at least about 0.2% to about 3%,
   wherein the components are present by weight, based on the total weight of the sunscreen composition.

4. The sunscreen composition according to claim 1, wherein:
   i. the C12-22 alkyl acrylate/hydroxyethylacrylate copolymer is present at about 1.8%;
   ii. the zinc oxide is present at about 7%; and
   iii. the at least one nonionic surfactant selected from the group consisting of polyethylene glycol ethers, polyethylene glycol esters of fatty acids, and combinations thereof is present in a total amount of about 2%, wherein the components are present by weight, based on the total weight of the sunscreen composition.

5. The sunscreen composition according to claim 1, wherein the at least one nonionic surfactant comprises at least one of steareth-2 or steareth-20.

6. The sunscreen composition according to claim 1, further comprising one or more non-mineral UV filters selected from organic UV filters.

7. The sunscreen composition according to claim 1, further comprising one or more organic UV filters comprising homosalate, octisalate and octocrylene.

8. The sunscreen composition according to claim 7, wherein the at least one mineral UV filter comprises the zinc oxide present in an amount in the range from about 5% to about 10%, and wherein homosalate is present in an amount in the range from about 5% to about 15%, octisalate is present in an amount in the range from about 1% to about 7%, and octocrylene is present in an amount in the range from about 7% to about 15%, each present by weight based on the total weight of the sunscreen composition.

9. The sunscreen composition according to claim 1, further comprising one or a combination of additives selected from the group consisting of solvents, SPF boosters, humectants, skin care actives, oils, waxes, thickeners, preservatives, pH adjusters, chelating agents, viscosity adjusters, cooling agents, fillers, fragrances, dyes, pigments, and combinations thereof.

10. The sunscreen composition according to claim 1, further comprising one or more additives selected from the group consisting of glycerin, propanediol, ethylhexyl methoxycrylene, butyloctyl salicylate, dicaprylyl carbonate, dicaprylyl ether, isopropyl palmitate, diethylhexyl syringylidenemalonate, trisodium ethylenediamine disuccinate, hydroxyacetophenone, citric acid, coco-caprylate/caprate, Oryza sativa cera, candelilla wax, sunflower seed wax, carnauba wax, polyhydroxystearic acid, xanthan gum, chlorphenesin, and combinations thereof.

11. The sunscreen composition according to claim 1, wherein the sunscreen composition excludes one or more ingredients selected from the group consisting of gemini surfactants, anionic gelling agents, Aristoflex polymers, pigments, iron oxides, and combinations thereof.

12. A sunscreen composition comprising an oil-in-water emulsion of aqueous and oil phases, comprising:
   i. at least one or more lipophilic thickener comprising C12-22 alkyl acrylate/hydroxyethylacrylate copolymer;
   ii. at least one mineral UV filter including zinc oxide;
   iii. at least one or more nonionic surfactant consisting of steareth-20 or a mixture of steareth-2 and steareth-20;
   iv. at least one or more organic UV filters selected from the group consisting of homosalate, octisalate and octocrylene, and combinations thereof; and
   V. one or a combination of additives selected from the group consisting of glycerin, propanediol, ethylhexyl methoxycrylene, butyloctyl salicylate, dicaprylyl carbonate, dicaprylyl ether, isopropyl palmitate, diethylhexyl syringylidenemalonate, trisodium ethylenediamine disuccinate, hydroxyacetophenone, citric acid, coco-caprylate/caprate, Oryza sativa cera, candelilla wax, polyhydroxystearic acid, sunflower seed wax, carnauba wax, xanthan gum, chlorphenesin, and combinations thereof.

13. The sunscreen composition according to claim 12, wherein the sunscreen composition demonstrates emulsion structural stability wherein the sun screen composition does not exhibit signs of phase separation, or become inhomogeneous after up to 12 weeks in an ambient temperature in the range from about 25° C. up to and including about 45° C., and maintains processibility wherein the sun screen composition can be produced at commercial scale characterized by a production volume of at least 15 kilograms without loss of emulsion structural stability, and wherein the sunscreen composition demonstrates an SPF (in vivo) in a range from about 30 to about 55.

14. A sunscreen composition comprising an oil-in-water emulsion of aqueous and oil phases, comprising:

i. at least one or more lipophilic oil thickener comprising C12-22 alkyl acrylate/hydroxyethylacrylate copolymer, present at about 1.8%;

ii. at least one mineral UV filter including zinc oxide, the zinc oxide present at about 7%;

iii. at least one or more nonionic surfactant including steareth-20 or a mixture of steareth-2 and steareth-20, present in a total amount of about 2%;

iv. at least one or more organic UV filters, present in a total amount of about 18%; and V. one or a combination of ingredients selected from the group consisting of solvents, SPF boosters, humectants, skin care actives, oils, waxes, thickeners, preservatives, pH adjusters, chelating agents, viscosity adjusters, cooling agents, fillers, fragrances, dyes, pigments, and combinations thereof, each present by weight, based on the total weight of the sunscreen composition.

15. The sunscreen composition according to claim 14, wherein the sunscreen composition excludes one or more ingredients selected from the group consisting of gemini surfactants, anionic gelling agents, Aristoflex polymers, pigments, iron oxides, and combinations thereof, and wherein the sunscreen composition demonstrates emulsion structural stability, and wherein the sun screen composition does not exhibit signs of phase separation, or become inhomogeneous after up to 12 weeks in an ambient temperature in the range from about 25° C. up to and including about 45° C., and maintains processibility wherein the sun screen composition can be produced at commercial scale characterized by a production volume of at least 15 kilograms without loss of emulsion structural stability, and wherein the sunscreen composition demonstrates an SPF in a range from about 30 to about 55.

16. The sunscreen composition according to claim 1, wherein the at least one lipophilic oil thickener is disposed entirely within and thickening the oil phase of the sunscreen composition.

17. The sunscreen composition according to claim 1, wherein the sunscreen composition is free of surfactants other than steareth-2 and steareth-20.

\* \* \* \* \*